(12) United States Patent
Liang et al.

(10) Patent No.: US 11,639,516 B2
(45) Date of Patent: May 2, 2023

(54) **HYDROXYTYROSOL STURGEON SKIN GELATIN FILM WITH ANTIOXIDANT ACTIVITY AND *SALMONELLA* DETECTION ABILITY AND A METHOD OF PREPARING THE SAME**

(71) Applicants: Chengyuan Liang, Xi'an (CN); Qi Lu, Xi'an (CN); Liang Xin, Xi'an (CN); Guaiping Qiao, Xi'an (CN); Jingyi Li, Xi'an (CN); Kangxiong Wu, Xi'an (CN); Han Li, Xi'an (CN); Bin Tian, Xi'an (CN)

(72) Inventors: Chengyuan Liang, Xi'an (CN); Qi Lu, Xi'an (CN); Liang Xin, Xi'an (CN); Guaiping Qiao, Xi'an (CN); Jingyi Li, Xi'an (CN); Kangxiong Wu, Xi'an (CN); Han Li, Xi'an (CN); Bin Tian, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 593 days.

(21) Appl. No.: 16/752,573

(22) Filed: Jan. 24, 2020

(65) Prior Publication Data
US 2021/0180104 A1    Jun. 17, 2021

(30) Foreign Application Priority Data
Dec. 17, 2019   (CN) .......................... 201911301048.5

(51) Int. Cl.
*C12Q 1/04* (2006.01)
*C07K 14/78* (2006.01)

(52) U.S. Cl.
CPC ................ *C12Q 1/04* (2013.01); *C07K 14/78* (2013.01); *C12Q 2304/20* (2013.01)

(58) Field of Classification Search
None
See application file for complete search history.

(56) References Cited

U.S. PATENT DOCUMENTS

2019/0031840 A1    1/2019   Liang et al.

FOREIGN PATENT DOCUMENTS

| JP | 2019110899 A | | 7/2019 |
|---|---|---|---|
| WO | 2013/101590 | * | 7/2013 |
| WO | 2015020138 A1 | | 2/2015 |
| WO | 2017094654 A1 | | 6/2017 |

* cited by examiner

*Primary Examiner* — Erin M. Bowers (57) ABSTRACT

A method of preparing a hydroxytyrosol sturgeon skin gelatin film with antioxidant activity and *Salmonella* detection ability includes: (1) mixing a neutral red indicator solution and distilled water at room temperature to obtain a mixture solution, and adding 1 mol/L $NaHCO_3$ solution to the mixture solution until discoloration to obtain an alkaline solution; (2) adding an amount of the alkaline solution obtained in step (1) to a mixture of Sturgeon skin gelatin and distilled water to obtain an alkaline gelatin solution; (3) adding hydroxytyrosol and glycerin and propylene glycol to the alkaline gelatin solution to obtain a hydroxytyrosol gelatin solution, and heating the hydroxytyrosol gelatin solution at 40-70° C.; (4) ultrasonicating the hydroxytyrosol gelatin solution from step (3), placing the hydroxytyrol gelatin solution evenly on a clean plexiglass plate, drying the hydroxytyrol gelatin solution on an ultra-clean worktable to obtain the hydroxytyrosol sturgeon skin gelatin film.

7 Claims, 5 Drawing Sheets

Blank reference surface (Example 1)

FIG.1 Blank reference surface (Example 1)

FIG. 2 Blank reference cross section (Example 1)

FIG. 3 Sample surface of hydroxycaseol film (Example 1)

FIG. 4 Sample cross section of hydroxycaseol film (Example 1)

FIG. 5 Thin film FTIR atlas (blank film and sample film both from Example 1)

FIG. 6 Thermogravimetric determination of (TGA) curve (Example 1)

FIG. 7 Schematic Diagram of Contact Angle (Example 1)

Control (Example 1, uninfected)

Sample (Example 1, after infection)

FIG. 8 Bacteriological Detection Diagram of Thin Film

HYDROXYTYROSOL STURGEON SKIN GELATIN FILM WITH ANTIOXIDANT ACTIVITY AND *SALMONELLA* DETECTION ABILITY AND A METHOD OF PREPARING THE SAME

The present invention claims priority to Chinese Patent Application No. 201911301048.5, filed on Dec. 17, 2019, which is incorporated by reference for all purposes as if fully set forth herein.

FIELD OF THE INVENTION

The invention relates to the field of food packaging, specifically, a hydroxytyrosol sturgeon skin gelatin film with antioxidative activity and *Salmonella* detection ability and a method of preparing the hydroxytyrosol sturgeon skin gelatin film.

BACKGROUND OF THE INVENTION

To have sustainable development, the effective use of environmental resources has become a hot topic in today's society. The packaging safety of food and medicine has also attracted people's attention. The use of non-toxic and degradable green packaging materials has become an important research area in the field of food packaging materials. Gelatin is obtained by the hydrolysis of collagen, and has good film forming ability and gas barrier property and of oxidation resistance, biocompatibility and biodegradability, an ideal packaging film material. At the same time, the development of the aquatic product processing industry has led to an increase in the amount of waste, such as fish skin. If it is used, it not only reduces the waste of resources, but also plays a role in protecting the environment. It also fully utilizes the excellent property of the fish skin. The development of fish skin and fish skin gelatin products has become popular.

Hydroxytyrosol is an active ingredient in olives. It has been found that hydroxytyrosol has anti-inflammatory, dilated blood vessels, antibacterial, anti-atherosclerosis and anti-cancer effects, especially the antioxidant activity of hydroxytyrosol. Therefore, the present invention intends to add hydroxytyrosol to the sturgeon skin gelatin film to further enhance the oxidation resistance of the film.

*Salmonella* is a gram-negative, blunt-ended *Bacillus brevis*. The use of routine testing procedures for *Salmonella* is complicated, time-consuming and laborious. Therefore, the establishment of a rapid and accurate detection method is needed. In the test for *Salmonella*, the propylene glycol and neutral red are added to the culture medium, and *Salmonella* can decompose propylene glycol to produce acid, and the neutral red indicator turns red. This leads the rapid identification of *Salmonella*.

The invention uses the less studied sturgeon skin gelatin film. Hydroxytyrosol is added to the sturgeon skin gelatin solution, and hydroxytyrosol sturgeon skin gelatin film is then prepared by a membrane liquid plate laying method. Experimental results show that hydroxytyrosol can significantly enhance the antioxidant effect of sturgeon skin gelatin film, and can effectively improve the mechanical properties of sturgeon skin gelatin film. Further, the method of detecting *Salmonella*-specific decomposition of propylene glycol to produce acid is applied to a food packaging film to prepare a hydroxytyrosol sturgeon skin gelatin film, which can be used for rapid detection of *Salmonella*. A packaging material is developed, which is not only beneficial to the preservation and storage of food, but also can quickly and accurately judge whether the food or drug is contaminated by *Salmonella*. Hydroxytyrosol-containing sturgeon skin gelatin film has broad application in in food packaging.

SUMMARY OF THE INVENTION

In one embodiment, a method of preparing a hydroxytyrosol sturgeon skin gelatin film with antioxidant activity and *Salmonella* detection ability includes the following steps: (1) mixing a neutral red indicator solution and distilled water at room temperature in a ratio of 1:65 to 1:70 (v:v) to obtain a mixture solution, and adding 1 mol/L $NaHCO_3$ solution to the mixture solution until discoloration to obtain an alkaline solution; (2) adding an amount of the alkaline solution obtained in step (1) to a mixture of Sturgeon skin gelatin and distilled water in a ratio of Sturgeon skin gelatin:distilled water=1:8 to 1:12 (w:w) to obtain an alkaline gelatin solution; (3) adding hydroxytyrol and glycerin in a ratio of Sturgeon skin gelatin:hydroxytyrol:glycerin=1:0.3:0.2 to 1:0.6:0.4 (w:w:w) and propylene glycol to the alkaline gelatin solution to obtain a hydroxytyrol gelatin solution, and heating the hydroxytyrol gelatin solution at 40-70° C.; (4) ultrasonicating the hydroxytyrol gelatin solution from step (3), placing the hydroxytyrol gelatin solution evenly on a clean plexiglass plate, drying the hydroxytyrol gelatin solution on an ultra-clean worktable at room temperature to obtain the hydroxytyrosol sturgeon skin gelatin film.

In another embodiment, the neutral red indicator solution includes neutral red and ethanol in a ratio of 5:95 (w:w).

In another embodiment, the ratio of neutral red indicator solution to distilled water is 1:67 (v:v).

In another embodiment, the ratio of the alkaline solution to the mixture of the Sturgeon skin gelatin and distilled water is 1:100 (v:v).

In another embodiment, the ratio of the Sturgeon skin gelatin and distilled water is 1:10 (w:w).

In another embodiment, the ratio of the sturgeon skin gelatin:hydroxytyrosol:glycerin is 1:0.4:0.3 (w:w:w).

In another embodiment, the hydroxytyrol gelatin solution at heated at 60° C.

In one embodiment, a hydroxytyrosol sturgeon skin gelatin film with antioxidant activity and *Salmonella* detection ability is prepared according to the method of claim 1.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Reference will now be made in detail to embodiments of the present invention, example of which is illustrated in the accompanying drawings. The following examples illustrate the present invention, but the present invention is not limited to the following examples.

Example 1

The example uses 706 g olive leaf and 235 g sturgeon skin as starting materials. The method of preparing a hydroxytyrosol Sturgeon skin gelatin film includes the following steps:

(1) Preparation of hydroxytyrosol: 706 g olive leaf powder was added to 3530 mL of 0.2 M hydrochloric acid solution. The solution was heated at 80° C. in a water bath for 4 h, neutralized to neutral with 2 M sodium hydroxide, and centrifugated to collect a filtrate. The filtrate was concentrated, and the concentrated filtrate, diluted with 4 times warm water, was purified by a macroporous resin, the eluent being 45% ethanol and the flow rate being 1.5 BV. The eluent was evaporated and concentrated, and 4 times the amount of methanol was added for recrystallization at 60° C. to obtain a crude product of hydroxytyrosol, 20 g, a yield of 2.83%.

Hydroxytyrosol (2) Preparation of sturgeon skin gelatin: 235 g sturgeon skin was mixed with 0.1 M NaOH solution containing 1% $H_2O_2$ (v/v) to form a mixture with a sturgeon skin/alkali solution ratio of 1/20 (w/v). The mixture was stirred at the speed of 400 rpm at room temperature for 24 hours, and the alkali solution was changed every 8 hours. The alkali treated fish skin was defatted with 10% isopropanol (v/v) for 4 hours, and washed with ice water to neutral or weakly alkaline. The defatted sturgeon skin was soaked in 0.05 M acetic acid at 4° C. with a sturgeon skin/acid solution ratio of 1:10 (w/v) for 4 hours, gently stirred, washed with distilled water to neutral, and then immersed in 10 times the amount of distilled water (w/v). The treated sturgeon skin was continuously stirred until sturgeon skin gelatin was extracted. The gelatin solution was centrifuged at room temperature for 30 minutes, and the supernatant was concentrated and freeze-dried and stored at 4° C. The sturgeon skin gelatin was 50 g, a yield of 21.28%.

(3) Preparation of hydroxytyrosol sturgeon skin gelatin film: 7 mL of the neutral red indicator solution was added to 500 mL water, and an appropriate amount of 1 M $NaHCO_3$ solution of was added. 50 g sturgeon skin gelatin obtained in step (2) was added to the solution and stirred evenly. The resulted solution was kept for 3-4 hours. After the solution was full swollen, 20 g hydroxytyrosol, 15 mL glycerol and an appropriate amount of propylene glycol were added, stirred continuously at 60° C. for 30 min, and then filtered with double-layer filter paper. The filtrate was treated by ultrasonic defoaming, spread out evenly on a clean plexiglass plate (15×15 $cm^2$), and dried in a ventilated oven at 25° C. and 50±5% relative humidity (RH) for 24 hours. The dried film (hydroxytyrosol sturgeon skin gelatin film) was peeled off by hand and stored in a dryer hydroxytyrosol sturgeon skin gelatin film.

Example 2

The example uses 706 g olive leaf and 235 g sturgeon skin as starting materials. The method of preparing a hydroxytyrosol Sturgeon skin gelatin film includes the following steps:

(1) Preparation of hydroxytyrosol: 706 g olive leaf powder was added to 3530 mL of 0.2 M hydrochloric acid solution. The solution was heated at 80° C. in a water bath for 4 h, neutralized to neutral with 2 M sodium hydroxide, and centrifugated to collect a filtrate. The filtrate was concentrated, and the concentrated filtrate, diluted with 4 times warm water, was purified by a macroporous resin, the eluent being 45% ethanol and the flow rate being 1.5 BV. The eluent was evaporated and concentrated, and 4 times the amount of methanol was added for recrystallization at 60° C. to obtain a crude product of hydroxytyrosol, 20 g, a yield of 2.83%.

(2) Preparation of sturgeon skin gelatin: 235 g sturgeon skin was mixed with 0.1 M NaOH solution containing 1% $H_2O_2$ (v/v) to form a mixture with a sturgeon skin/alkali solution ratio of 1/20 (w/v). The mixture was stirred at the speed of 400 rpm at room temperature for 24 hours, and the alkali solution was changed every 8 hours. The alkali treated fish skin was defatted with 10% isopropanol (v/v) for 4 hours, and washed with ice water to neutral or weakly alkaline. The defatted sturgeon skin was soaked in 0.05 M acetic acid at 4° C. with a sturgeon skin/acid solution ratio of 1:10 (w/v) for 4 hours, gently stirred, washed with distilled water to neutral, and then immersed in 10 times the amount of distilled water (w/v). The treated sturgeon skin was continuously stirred until sturgeon skin gelatin was extracted. The gelatin solution was centrifuged at room temperature for 30 minutes, and the supernatant was concentrated and freeze-dried and stored at 4° C. The sturgeon skin gelatin was 50 g, a yield of 21.28%.

(3) Preparation of hydroxytyrosol sturgeon skin gelatin film: 7 mL of the neutral red indicator solution was added to 500 mL water, and an appropriate amount of 1 M $NaHCO_3$ solution of was added. 50 g sturgeon skin gelatin obtained in step (2) was added to the solution and stirred evenly. The resulted solution was kept for 3-4 hours. After the solution was full swollen, 20 g hydroxytyrosol, 15 mL glycerol and an appropriate amount of propylene glycol were added, stirred continuously at 50° C. for 30 min, and then filtered with double-layer filter paper. The filtrate was treated by ultrasonic defoaming, spread out evenly on a clean plexiglass plate (15×15 $cm^2$), and dried in a ventilated oven at 25° C. and 50±5% relative humidity (RH) for 24 hours. The dried film (hydroxytyrosol sturgeon skin gelatin film) was peeled off by hand and stored in a dryer hydroxytyrosol sturgeon skin gelatin film.

Example 3

The example uses 706 g olive leaf and 235 g sturgeon skin as starting materials. The method of preparing a hydroxytyrosol Sturgeon skin gelatin film includes the following steps: (1) Preparation of hydroxytyrosol: 706 g olive leaf powder was added to 3530 mL of 0.2 M hydrochloric acid solution. The solution was heated at 80° C. in a water bath for 4 h, neutralized to neutral with 2 M sodium hydroxide, and centrifugated to collect a filtrate. The filtrate was concentrated, and the concentrated filtrate, diluted with 4 times warm water, was purified by a macroporous resin, the eluent being 45% ethanol and the flow rate being 1.5 BV. The eluent was evaporated and concentrated, and 4 times the amount of methanol was added for recrystallization at 60° C. to obtain a crude product of hydroxytyrosol, 20 g, a yield of 2.83%.

(2) Preparation of sturgeon skin gelatin: 235 g sturgeon skin was mixed with 0.1 M NaOH solution containing 1% $H_2O_2$ (v/v) to form a mixture with a sturgeon skin/alkali solution ratio of 1/20 (w/v). The mixture was stirred at the speed of 400 rpm at room temperature for 24 hours, and the alkali solution was changed every 8 hours. The alkali treated fish skin was defatted with 10% isopropanol (v/v) for 4 hours, and washed with ice water to neutral or weakly alkaline. The defatted sturgeon skin was soaked in 0.05 M acetic acid at 4° C. with a sturgeon skin/acid solution ratio of 1:10 (w/v) for 4 hours, gently stirred, washed with distilled water to neutral, and then immersed in 10 times the amount of distilled water (w/v). The treated sturgeon skin was continuously stirred until sturgeon skin gelatin was extracted. The gelatin solution was centrifuged at room temperature for 30 minutes, and the supernatant was concentrated and freeze-dried and stored at 4° C. The sturgeon skin gelatin was 50 g, a yield of 21.28%.

(3) Preparation of hydroxytyrosol sturgeon skin gelatin film: 7 mL of the neutral red indicator solution was added to 500 mL water, and an appropriate amount of 1 M $NaHCO_3$ solution of was added. 50 g sturgeon skin gelatin obtained in step (2) was added to the solution and stirred evenly. The resulted solution was kept for 3-4 hours. After the solution was full swollen, 20 g hydroxytyrosol, 15 mL glycerol and an appropriate amount of propylene glycol were added, stirred continuously at 70° C. for 30 min, and then filtered with double-layer filter paper. The filtrate was treated by ultrasonic defoaming, spread out evenly on a clean plexiglass plate (15×15 $cm^2$), and dried in a ventilated oven at 25° C. and 50±5% relative humidity (RH) for 24 hours. The dried film (hydroxytyrosol sturgeon skin gelatin film) was peeled off by hand and stored in a dryer hydroxytyrosol sturgeon skin gelatin film.

By comparing the hydroxytyrosol sturgeon skin gelatin films prepared by the above Examples 1-3, the condition of Example 1 is preferred.

Example 4

Hydroxytyrol Sturgeon Skin Gelatin Film Antioxidant Activity Measurement—DPPH Method.

First, the hydroxytyrosol sturgeon skin gelatin film of Example 1 was dissolved in 5% SDS and kept in a water bath at 85° C. for 1 h, and then the insoluble fragments were removed by centrifugation 5 min at room temperature. 1.5 mL of film solution and 1 mL of 95% ethanol were mixed with 1.5 mL 0.1 M DPPH solution, and the mixture was fully mixed and reacted with 30 min at room temperature. The mixture was concentrated at 8000×g for 5 minutes. The mixture's absorbance Ai at 517 nm was measured by a spectrophotometer. The absorbance Aj of 1.5 mL of 95% ethanol mixed with 1.5 mL film solution and the absorbance Ao of 1.5 mL of 95% ethanol mixed with 0.1 M DPPH solution were also measured. Cowhide gelatin film was used as a comparison. The antioxidant activity of cowhide gelatin film was determined by DPPH clearance method, and the scavenging rate was calculated by spectrophotometry according to the change of absorbance. The DPPH radical scavenging activity was calculated as follows:

Clearance rate $(\%) = [1-(A_i-A_j)/A_0] \times 100\%$

DPPH test results are shown in Table 1.

TABLE 1

| | Absorbance determination | | | |
|---|---|---|---|---|
| Sample | $A_0$ | $A_i$ | $A_j$ | Clearance |
| Hydroxytyrosol sturgeon skin | 0.484 | 0.412 | 0.088 | 33.1% |
| Cowhide gelatin film | 0.484 | 0.463 | 0.076 | 20.0% |

As shown in Table 1 above, the clearance rate of hydroxytyrosol sturgeon skin gelatin film was 33.1%, and that of cowhide gelatin film was 20.0%. Therefore, the antioxidant activity of hydroxytyrosol sturgeon skin gelatin film was higher than that of cowhide gelatin film.

Example 5

Hydroxytyrol Sturgeon Skin Gelatin Film Antioxidant Activity Measurement-Reduction Method In an acidic solution, a reducing substance reacts with potassium ferricyanide to produce potassium ferrocyanide. Fe' then reacts with potassium ferricyanide (high concentration) to produce soluble Prussian blue. Prussian blue can be measured by the absorbance at 700 mm. Higher absorbance at 700 mm indicates greater reduction ability of the substance.

The aqueous solution of 2 mL hydroxytyrosol sturgeon skin gelatin film of Example 1 was added into 2.5 mL 0.2 M phosphate buffer (pH 6.6) and 2.5 mL 1% potassium ferricyanide. The mixture reacted for 20 minutes at 50° C. and added 2.5 mL 10% trichloroacetic acid. The mixture reacted at 50° C. for 20 minutes, and then centrifuged at 2000×g and 22° C. for 10 min. The supernatant (2.5 mL) was mixed with 2.5 mL deionized water and 0.5 mL 0.1% ferri-chloride. After the reaction of 10 minutes, the absorbance of the solution was measured under 700 nm. A thin film solution containing 1.0 mg/mL vitamin C was used as the positive control. The higher the absorbance, the stronger the reduction ability. The absorbance of the film solution and the control film solution containing vitamin C was measured for three times, and the average value was taken as the absorbance value. The results are shown in Table 2.

TABLE 2

| | Absorbance at 700 mm | | | |
|---|---|---|---|---|
| Sample | $A_1$ | $A_2$ | $A_3$ | A(average) |
| Hydroxytyrosol sturgeon skin gelatin film | 0.147 | 0.146 | 0.148 | 0.147 |

TABLE 2-continued

Absorbance at 700 mm

| Sample | $A_1$ | $A_2$ | $A_3$ | A(average) |
|---|---|---|---|---|
| Thin film solution containing vitamin C | 0.175 | 0.174 | 0.176 | 0.175 |

Table 2 shows that the antioxidant activity of the sample is close to that of the film solution containing 1.0 mg/mL vitamin C, which indicates that the hydroxytyrosol sturgeon skin gelatin film has a good reduction effect.

Example 6

Hydroxytyrosol Sturgeon Skin Gelatin Film Thickness Measurement

The thickness of the hydroxytyrosol sturgeon skin gelatin film of Example 1 was measured by a thickness meter, and the thickness of the film sample at 5 random positions was measured, and the average value was taken as the thickness value. The thickness measurement results are shown in Table 3.

TABLE 3

Film thickness measurement

| Thicknes | Measurement ($10^{-2}$ mm) | | | | | Average ($10^{-2}$ mm) |
|---|---|---|---|---|---|---|
| $d_1$ | 5.1 | 5.2 | 5.1 | 5.3 | 4.9 | 5.12 |
| $d_2$ | 4.9 | 4.9 | 5.2 | 5.3 | 5.1 | 5.08 |
| $d_3$ | 4.8 | 5.3 | 5.4 | 4.9 | 4.7 | 5.02 |

Overall: $d=(d_1+d_2+d_3)/3=5.07\times10^{-2}$ mm

In the experiment, the plexiglass plate was placed on a super-clean worktable. A toppling method was used to make the prepared gelatin solution expand evenly on the flat plate. The thickness difference of the five random positions of the film is about 0.007 mm, which indicates that the thickness of the film is uniform and smooth.

Example 7

Hydroxytyrosol Sturgeon Skin Gelatin Film Mechanical Properties Measurement

The mechanical properties of the film depend on the molecular weight, cross-linking degree, solvent and plasticizer content of the membrane material. The mechanical properties of the film are mainly reflected by the tensile strength (TS) and elongation at break (EAB). TS is an index that reflects the strength of the film, while EAB reflects the plasticity of the film. The hydroxytyrosol sturgeon skin gelatin film of Example 1 was placed at room temperature and 50±5% RH for 72 h. Eight film samples (2×5 cm$^2$) with initial grip length of 3 cm were prepared to test their mechanical properties. The average thickness of each film sample was used to estimate the cross-sectional area. The initial clamping separation and mechanical crosshead velocity of the film were set to 30 mm/min. TS and EAB are calculated using maximum load and final fracture extension. Sturgeon skin gelatin film without hydroxytyrosol was used as a blank control.

The specific calculation formula is as follows:

$$TS=Fm/(d_O\times W)$$

In the formula: TS: tensile strength (MPa); Fm: Maximum tension on fracture of specimen (N); d: Thickness of thin film (mm); W: Film width (mm).

$$EAB=(\Delta L/L_O)\times100\%=[(L_1-L_O)/L_O]\times100\%$$

In the formula: $L_O$: The original length of the film (mm); $\Delta L$: the length stretched when the film is broken (mm); $L_1$: the maximum length reached when the film is broken (mm).

The TS and EAB results of the hydroxytyrosol sturgeon skin gelatin film prepared in Example 1 are shown in Table 4.

TABLE 4

Film mechanical properties measurement

| Sample | | Measurement | | | | | | | | Average |
|---|---|---|---|---|---|---|---|---|---|---|
| Hydroxytyrosol Sturgeon skin gelatin film | TS (Mpa) | 34.86 | 34.83 | 34.91 | 34.92 | 34.89 | 34.87 | 34.85 | 34.88 | 34.876 |
|  | EAB(%) | 6.28 | 6.24 | 6.22 | 6.32 | 6.35 | 6.29 | 6.31 | 6.25 | 6.283 |
| Sturgeon skin gelatin film | TS(Mpa) | 30.54 | 30.48 | 30.52 | 30.53 | 30.64 | 30.62 | 30.61 | 30.59 | 30.566 |
|  | EAB(%) | 5.52 | 5.48 | 5.49 | 5.54 | 5.58 | 5.57 | 5.53 | 5.59 | 5.538 |

As shown in Table 4, the mechanical properties of Sturgeon skin gelatin film with hydroxytyrosol are better than that of Sturgeon skin gelatin film without hydroxytyrosol.

Example 8

Hydroxytyrosol Sturgeon Skin Gelatin Film Water Solubility Measurement

The hydroxytyrosol sturgeon skin gelatin film sample of Example 1 (3×2 cm$^2$) was dried at 105° C. for 24 h and weighed ($W_1$). Then the film was immersed in 15 mL distilled water and placed in an oscillating water bath at 25° C. After 24 hours, the coagulated film was removed, dried (105° C., 24 hours) and weighed ($W_2$). The sturgeon skin gelatin film without hydroxytyrosol was used as a blank control. The weight of dissolved dry matter was calculated as follows:

$$WS(\%)=(W_1-W_2)\times100/W_1$$

The solubility of hydroxytyrosol sturgeon skin gelatin film prepared in Example 1 was 74.26±0.18%, and that of sturgeon skin gelatin film without hydroxytyrol was 89.49±0.25%. The results showed that the sturgeon skin gelatin film with hydroxytyrosol was generally water-soluble and suitable for food packaging materials with low water content.

Example 9

Hydroxytyrol Sturgeon Skin Gelatin Film Water Vapor Transmittance Measurement

The water vapor permeability coefficient of the film refers to the amount of steam passing through the unit thickness and unit area of the film in unit time and unit steam pressure difference. The water vapor permeability coefficient of the film is a very important parameter to measure the moisture permeability of the film. The smaller the water vapor permeability coefficient is, the less easy the water vapor is to pass through, and the better its water resistance is. Water vapor permeability coefficient is an index to measure the density of film structure.

The hydroxytyrosol sturgeon skin gelatin film sample prepared in Example 1 was sealed with silica gel vacuum grease and rubber gasket in a bottle containing dry silica gel (0% RH). The bottle is placed in a dryer containing distilled water, and the dried gelatin film is measured in a water vapor permeator.

The WVP value of the hydroxytyrosol sturgeon skin gelatin film prepared in Example 1 is $1.99\pm0.29\times10^{-10}$ g m$^{-1}$ Pa$^{-1}$ s$^{-1}$. The WVP value of sturgeon skin gelatin film without hydroxytyrosol was $2.65\pm0.07\times10^{-10}$ g m$^{-1}$ Pa$^{-1}$ s$^{-1}$. The results showed that the hydroxytyrosol sturgeon skin gelatin film was compact and had good waterproof performance.

Example 10

Hydroxytyrosol Sturgeon Skin Gelatin Film Light and Transparency Measurement

A mold sample with a smooth surface was selected from the gelatin film sample made in Example 1, cut it to a size of 4 cm×1 cm, attached to one side of the colorimetric dish (1 cm), placed in the sample pool of the UV-vis spectrophotometer, and measured for its absorbance at the 600 nm. Thus, the light transmittance and transparency of the thin film were calculated. Sturgeon skin gelatin film without hydroxytyrosol was used as a blank control.

The light transmittance and transparency of the hydroxytyrosol sturgeon skin gelatin film prepared in Example 1 at 600 nm wavelength were 83.31% and 2.49±0.03, respectively. The light transmittance of sturgeon skin gelatin film without hydroxytyrosol at 600 nm wavelength is 91.84%, and the transparency is 0.74±0.02. The experimental data show that the light transmittance of hydroxytyrosol sturgeon skin gelatin film is lower than that of sturgeon skin gelatin film without hydroxytyrosol. It has good light resistance, and the corresponding transparency is higher than that of sturgeon skin gelatin film without hydroxytyrosol, which can well reflect the original color and appearance of fresh food, and is suitable for food packaging.

Example 11

Figure 1:
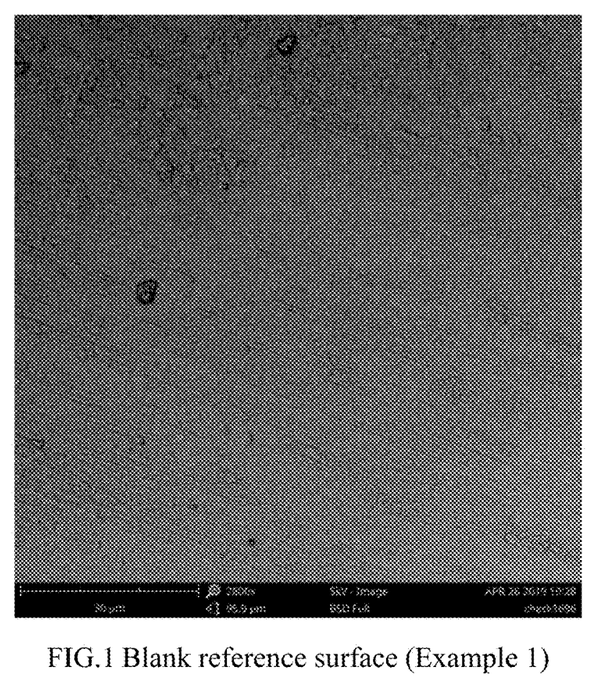
FIG. 1 is the SEM image of the surface structure of a sturgeon skin gelatin film.
Figure 2:
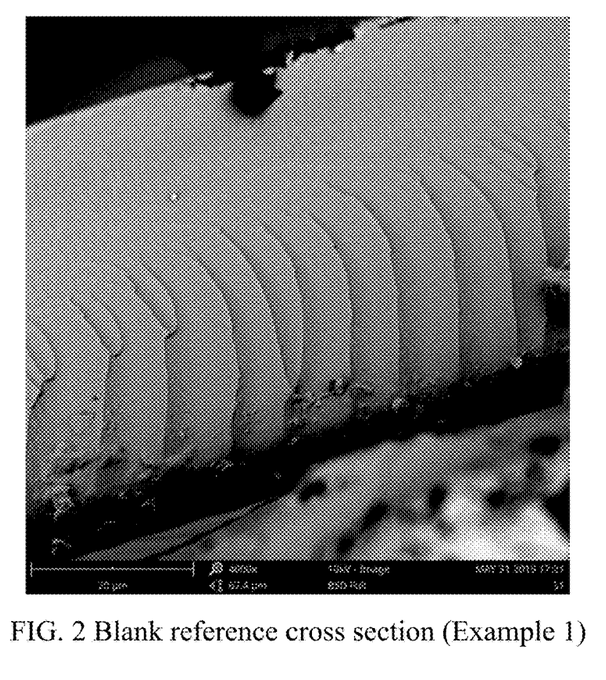
FIG. 2 is the SEM image of the cross-sectional structure of the sturgeon skin gelatin film.
Figure 3:
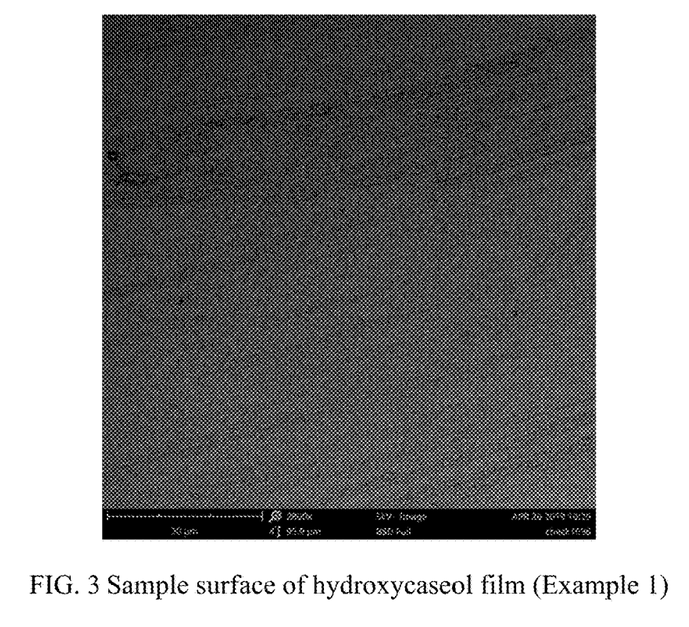
FIG. 3 is the SEM image of the surface structure of a hydroxytyrosol sturgeon skin gelatin film (Example 1).
Figure 4:
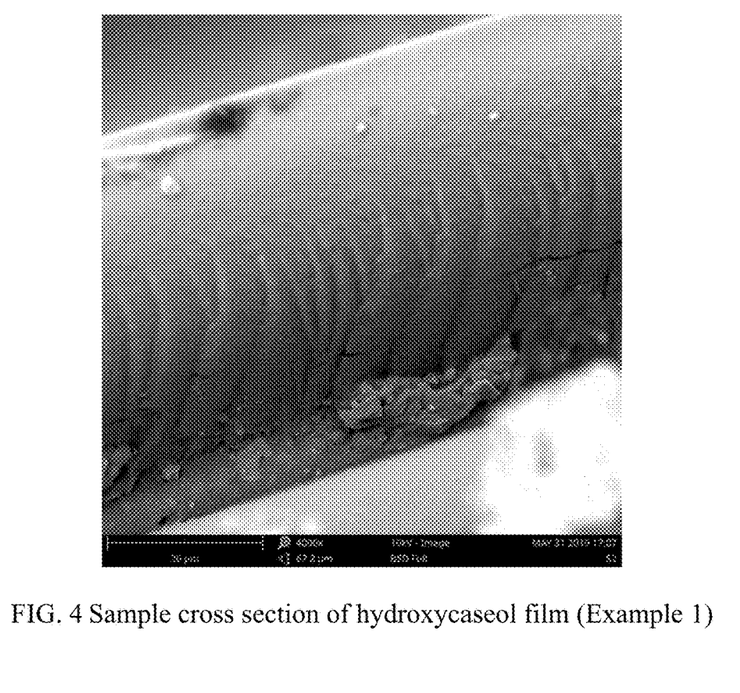
FIG. 4 is the SEM image of the cross-sectional structure of the hydroxytyrosol sturgeon skin gelatin film (Example 1).

Hydroxytyrosol Sturgeon Skin Gelatin Film Characterization (1) Film Microstructure Measurement Scanning electron microscope (SEM) analysis: the cross section of the thin film sample prepared in Example 1 was broken off in liquid nitrogen, the surface and cross section of the sample was affixed to the electron microscope table, and the gold spray treatment was carried out and placed under the scanning electron microscope. The surface and cross-section structure of the film was observed, and the sturgeon skin gelatin film without hydroxytyrosol was used as a blank control. FIG. 1 shows the surface of the blank reference substance. FIG. 2 shows the blank reference cross section. FIG. 3 shows the surface of a sample containing hydroxycaseol film. FIG. 4 shows a cross section of a sample containing hydroxycaseol film. The surface of the blank reference substance was smooth and uniform, there was no brittle area, and the molecules were arranged in an orderly manner. The micrographs of sturgeon skin gelatin film with hydroxytyrosol showed similar characteristics, and the surface was smoother and more uniform than that of the control group. For the fracture cross section, the film containing hydroxytyrosol showed a more compact structure than the control film, and there was no particle or obvious stratification phenomenon, indicating that the hydroxytyrosol sturgeon skin gelatin film is a uniform dispersion system, which can be used for food packaging and preservation.

(2) Fourier Transform Infrared Spectroscopy (FTIR)

Figure 5:
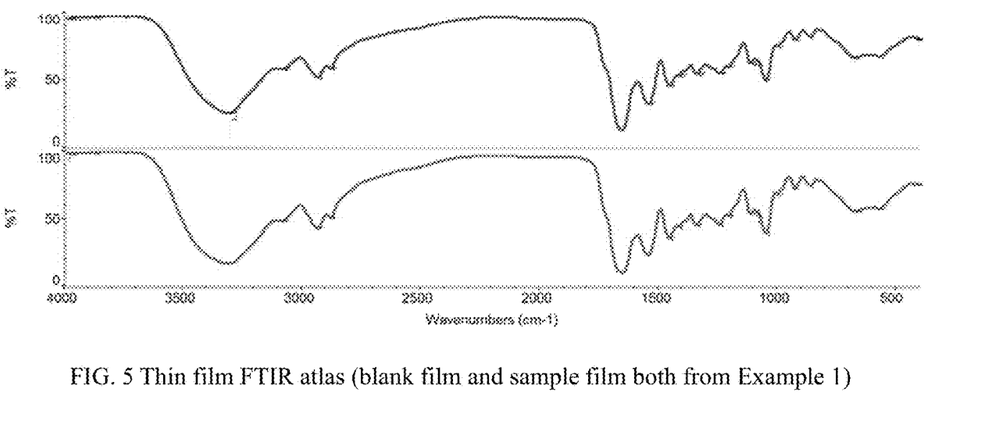
FIG. 5 is the Fourier-transform infrared (FTIR) spectroscopy of the hydroxytyrosol sturgeon skin gelatin film (Example 1).

The FTIR spectra of the hydroxytyrosol sturgeon skin gelatin film of Example 1 was measured by FTIR spectrometer. Before analysis, the film was placed at room temperature in a dryer containing $P_2O_5$ for 10 days to achieve maximum dehydration. In the range of 500-4000 cm$^{-1}$, 32 scans were performed with the resolution of 4 cm$^{-1}$, and the spectral images were collected automatically for analysis. FTIR spectra are used to monitor functional groups and structural changes in thin film samples at the molecular level.

3315.1 cm$^{-1}$ is the stretching vibration peak of N—H and OH;

1600 cm$^{-1}$: amide I band (stretching vibration peak of Corio and imine H).

1542.9 cm$^{-1}$: amide II band (NH bending vibration peak);

1240 cm$^{-1}$: amide III band (NH deformation peak);

1336 cm$^{-1}$: amide IV band, which is caused by the left and right swing of $CH_2$ on the side chain of proline.

1452 cm$^{-1}$ is the peak of N—H stretching or N—H deformation.

1045 cm$^{-1}$ is the stretching vibration peak of C—O—C and C—O—H.

The results of FTIR show that the addition of hydroxytyrosol enhanced the cross-linking with gelatin and formed a more compact membrane network.

(3) Thermogravimetric Analysis (TGA)

Before analysis, the hydroxytyrosol sturgeon skin gelatin film of Example 1 was placed in a dryer containing $P_2O_5$ at room temperature for 10 days. Using thermogravimetric analyzer, the dehydrated film was scanned from 20° C. to 600° C. at the rate of 10° C./min. Nitrogen was used as the purification gas and the flow rate was 20 mL/min. Table 4 shows the thermal degradation temperature (Td, Δ° C.) and weight loss (Δ w,%) of hydroxytyrosol sturgeon skin gelatin film.

TABLE 5

| | Film thermal degradation temperature (Td, Δ ° C.) and weight loss (Δ w, %) | | | | |
|---|---|---|---|---|---|
| | $\Delta_1$ | | $\Delta_2$ | | |
| | $Td_1$ | $\Delta w_1$ | $Td_2$ | $\Delta w_2$ | Residual (%) |
| Film | 98.6 | 9.89 | 397.5 | 39.74 | 24.28 |

Note:
$\Delta_1$, and $\Delta_2$ represent the weight loss of the first and second stages of the film, respectively.

Figure 6:
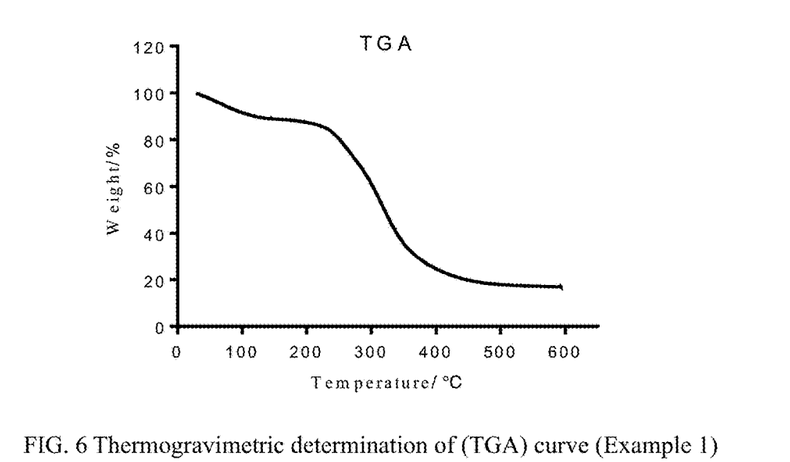
FIG. 6 shows the Thermal Gravimetric Analysis (TGA) results of the hydroxytyrosol sturgeon skin gelatin film (Example 1).

The TGA results are shown in FIG. 6. The gelatin film shows two main stages of weight loss. The first stage is between 51.2° C. and 98.6° C. The weight loss of gelatin film was slow and the weight was reduced by about 9.89%. The weight reduction of gelatin film may be composed of free water adsorbed by gelatin film, bound water of structure and glycerol propylene glycol. The second stage was between 198.4° C. and 397.5° C., and the weight was reduced by about 39.74%. This stage may be due to the degradation of molecular weight peptides and gelatin chains in the film. After 420° C., the thermal analysis curve changed little, and the protein basically decomposed completely. It is found that sturgeon skin gelatin films have good thermal stability, and the improvement of thermal stability can be well applied to the development of food packaging films.

Example 12

Hydroxytyrosol Sturgeon Skin Gelatin Film Hydrophobicity Measurement

Figure 7:
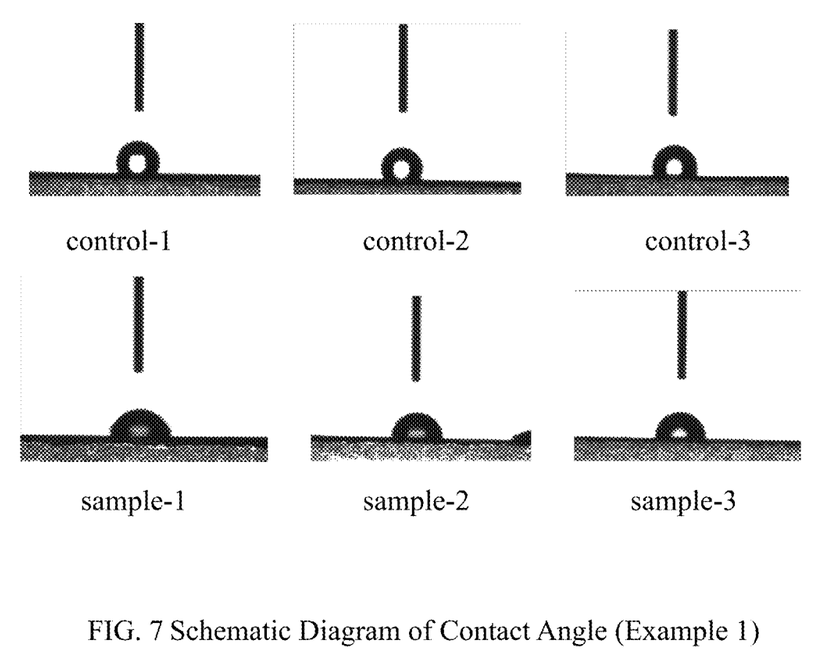
FIG. 7 shows the contact angles between the water droplets and the hydroxytyrosol sturgeon skin gelatin film (Example 1).

The hydroxytyrosol sturgeon skin gelatin film of Example 1 was cut into a rectangular sample of the size of 0.5 cm×5cm and fixed on a flat and clean glass sheet. The contact angle between the water droplet and the thin film was measured by a video optical contact angle tester to determine the hydrophobic degree of the film. The water drop capacity was set to 5 μL, three drops were randomly selected on the thin film sample, the contact angle was recorded, and the average value was calculated. The results are shown in FIG. 7 and Table 6.

TABLE 6

Hydroxytyrosol Sturgeon Skin Gelatin Film Contact Angle

| Sample | Contact angle | | | Average |
|---|---|---|---|---|
| Sturgeon skin gelatin fim | 115.4 | 114.4 | 109 | 112.9 |
| Hydroxytyrosol sturgeon skin gelatin film | 90.9 | 92.7 | 96.9 | 93.5 |

Table 6 and FIG. 7 show that the contact angle of sturgeon skin gelatin film without hydroxytyrosol is more than 90° and is hydrophobic. The contact angle of hydroxytyrosol is reduced as a whole, but its contact angle is still more than 90°, which is hydrophobic and can be used in food packaging with a small amount of water.

Example 13

Hydroxytyrosol Sturgeon Skin Gelatin Film's *Salmonella* Detection Ability (1) Sturgeon skin gelatin film with hydroxytyrosol of Example 1 was tested for *Salmonella* detection ability. A Sturgeon skin gelatin film without hydroxytyrol was used as a blank control.

(2) *Salmonella* was placed in the test tubes with the same diameter as a turbidimetric tube, the aseptic distilled water was added, and the bacterial suspension with the same concentration as a No. 3 turbidimetric tube was prepared.

Figure 8:
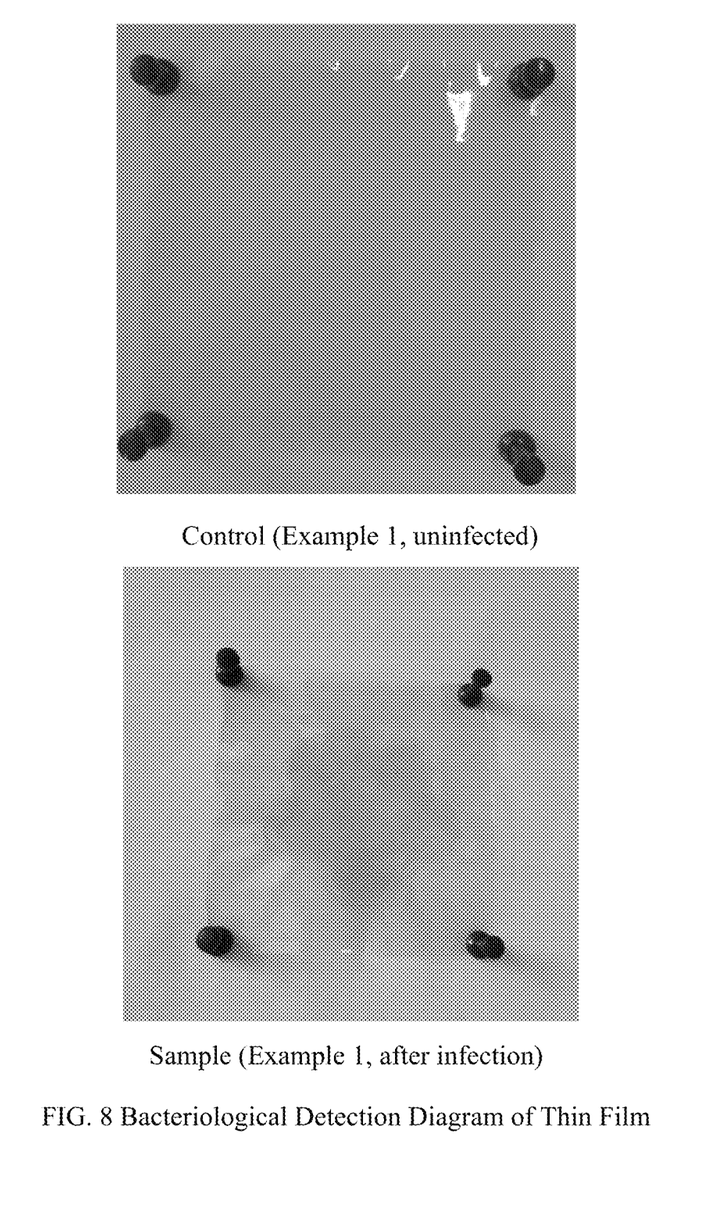
FIG. 8 shows the hydroxytyrosol sturgeon skin gelatin film's *Salmonella* detection ability.

(3) The prepared bacterial suspension was sprayed on the Sturgeon skin gelatin film with hydroxytyrosol of Example 1 and the Sturgeon skin gelatin film without hydroxytyrol. The films were observed for color change. The results are shown in FIG. 8.

After spraying bacterial solution on the film, the changes of the film were observed. As shown in FIG. 8, the film containing hydroxytyrosol, propylene glycol and neutral red changed from orange to purple red due to infection with *Salmonella*, indicating that *Salmonella* decomposed propylene glycol to produce acid and turned neutral red to red. The results showed that this method was sensitive to the detection of *Salmonella*, and changed obviously before and after infection, so it was suitable for the rapid detection of *Salmonella*. There was no color change for the Sturgeon skin gelatin film without hydroxytyrol.

It is obvious to those skilled in the art that various modifications and changes can be made in the present invention without departing from the spirit or scope of the invention. Therefore, the object of the present invention is to cover modifications and variants of the invention, as long as they are within the scope of the attached claims and their equivalents.

What is claimed is:

1. A method of preparing a hydroxytyrosol sturgeon skin gelatin film with antioxidant activity and *Salmonella* detection ability comprising the following steps:
   (1) mixing a neutral red indicator solution and distilled water at room temperature in a ratio of 1:65 to 1:70 (v:v) to obtain a mixture solution, and adding 1 mol/L $NaHCO_3$ solution to the mixture solution until discoloration to obtain an alkaline solution;
   (2) adding an amount of the alkaline solution obtained in step (1) to a mixture of Sturgeon skin gelatin and distilled water in a ratio of Sturgeon skin gelatin:distilled water=1:8 to 1:12 (w:w) to obtain an alkaline gelatin solution;
   (3) adding hydroxytyrosol and glycerin in a ratio of Sturgeon skin gelatin:hydroxytyrosol:glycerin=1:0.3:0.2 to 1:0.6:0.4 (w:w:w) and propylene glycol to the alkaline gelatin solution to obtain a hydroxytyrosol gelatin solution, and heating the hydroxytyrosol gelatin solution at 40-70° C.;
   (4) ultrasonicating the hydroxytyrosol gelatin solution from step (3), placing the hydroxytyrosol gelatin solution evenly on a plexiglass plate, drying the hydroxytyrosol gelatin solution on a worktable at room temperature to obtain the hydroxytyrosol sturgeon skin gelatin film.

2. The method of claim 1, wherein the neutral red indicator solution includes neutral red and ethanol in a ratio of 5:95 (w:w).

3. The method of claim 1, wherein the ratio of neutral red indicator solution to distilled water is 1:67 (v:v).

4. The method of claim 1, wherein the ratio of the alkaline solution to the mixture of the Sturgeon skin gelatin and distilled water is 1:100 (v:v).

5. The method of claim 1, wherein the ratio of the Sturgeon skin gelatin and distilled water is 1:10 (w:w).

6. The method of claim 1, wherein the ratio of the sturgeon skin gelatin:hydroxytyrosol:glycerin is 1:0.4:0.3 (w:w:w).

7. The method of claim 1, wherein the hydroxytyrosol gelatin solution is heated at 60° C.

* * * * *